UNITED STATES PATENT OFFICE.

WILLIAM E. CRAIG, OF JOPLIN, MISSOURI, ASSIGNOR, BY MESNE ASSIGNMENTS, TO CRAIG CHEMICAL CORPORATION, OF CLEVELAND, OHIO, A CORPORATION OF DELAWARE.

TREATMENT FOR VENEREAL DISEASES.

15,411. Specification of Reissued Letters Patent. Reissued July 18, 1922.

No Drawing. Original No. 1,408,170, dated February 28, 1922, Serial No. 265,356, filed December 5, 1918. Application for reissue filed March 3, 1922. Serial No. 540,897.

*To all whom it may concern:*

Be it known that I, WILLIAM E. CRAIG, a citizen of the United States, residing at Joplin, in the county of Jasper and State of Missouri, have invented new and useful Improvements in Treatment for Venereal Diseases, of which the following is a specification.

This invention is characterized by being not only a treatment of but a proven cure for syphilis in any stage, the more virulent and advanced stages responding to the treatment and being cured with as much effectiveness as lighter and earlier conditions thereof, the essential difference in the treatment of different stages residing in variations in the degree of prolongation and strength of the remedy employed. The remedy is also valuable in the treatment of other venereal and germ diseases.

In this treatment, I employ opium, mercury, quinine, licorice, and a binder, and administer by the mouth and in solid form, preferably a tablet. The patient should be warned against the use of acids, but an accidental or slight use of acid foods usually will not be found injurious.

For mild or earlier stages of the disease, I administer as one dose for an adult two thirty-seconds of a grain of opium; thirty-two thirty-seconds of a grain of blue mass; ten thirty-seconds of a grain of sulphate of quinine, and ten thirty-seconds of a grain of licorice. This dose is given three times per day. For more virulent or advanced stages the same materials and number of doses are administered but strengthened by employing four thirty-seconds of a grain of opium; forty-eight thirty-seconds grain of blue mass; sixteen thirty-seconds of a grain of sulphate of quinine, and twenty thirty-seconds of a grain of licorice. For children, the dose should be reduced proportionally to the age within the discretion of the physician, and in instances where it is difficult to get a child to take the medicine in the form of a solid, the physician may crush the tablet, or such fraction thereof as he determines should be used as a dose, and give it in water. Tablets may be specially made softer or more friable to facilitate this operation.

I am able to administer this remedy as a continuous treatment without cessation up to the point of complete cure; and in all of the cases which I have treated I have not had a single instance of mercuric poisoning.

For convenience of reference, I have called the lighter treatment No. 1, and the stronger treatment No. 2. Presented as formulæ, these two treatments are preferably prepared as follows:

*No. 1.*

Pulverized opium, grains II.
Pulvis pill hydrarge, grains XXXII.
Quinine sulphate, grains X.
Licorice powder, grains X.
Extract malt, Qs. mass.
M. ft. tablets, XXXII.
Signature: One three times daily.

The abbreviation "Qs.", as is well known to the profession, is employed to signify "quantity sufficient".

*No. 2.*

Pulverized opium, grains IV.
Pulvis pill hydrarge, grains XLVIII.
Quinine sulphate, grains XVI.
Licorice powder, grains XX.
Extract malt, Qs. mass.
M. ft. tablets, XXXII.
Signature: One three times daily.

It should be understood that pulvis pill hydrarge (blue mass) is preferably employed because of its accessibility, but, of course, it is to be understood that the same or similar results may be obtained by the utilization of mercury in the same or substantially the same quantities even if otherwise prepared and employed with other dilutent, so long as not presented in a form either injurious to the patient or failing to have the requisite therapeutical action.

It will also be noted that in each of the formulæ above given, there is included sufficient malt to make a pill mass, and the malt serves as a binder, facilitating the production of tablets. Any appropriate substitutes may be utilized for this binder.

The actual steps of the operation of preparing the remedy consistent with the two above-quoted formulæ are the same in both cases and may be stated as follows:

First weigh out the quinine, then the amount of pulverized opium and thoroughly triturate them; then add the pulvis pill hydrarge, and then thoroughly triturate again; then add the licorice powder and again thoroughly triturate until all ingredients are thoroughly mixed; then add sufficient extract of malt to make a pill mass. After this process is completed, the compound is put into a bake oven and baked until it is thoroughly dried sufficiently to be converted into a powder. This powder is then run through a sieve and is then ready for the tablet machine.

The bowels should be caused to move at least once a day during treatment, and, if necessary, the patient should take a laxative to effect this result and to avoid any accumulation of mercury, and at the same time prevent touching up of the gums or salivation. Also the physician will understand that in the interest of sanitation and for the comfort of the patient, a palliative treatment for any local irritation should be employed to avoid further impregnation or irritation, as by the cleansing of a sore or sores and touching it or them with nitrate of silver or other germicidal agent.

The continuation of the treatment depends largely on the improvement and the idiosyncrasy of the patient, and the length of time that has elapsed since the initial lesion of the disease. An ordinary case will show marked improvement in two or three weeks, but the remedy should be continued from three, six to twelve months. The length of treatment is governed largely by the results as shown by the blood tests.

While I am able to demonstrate the effectiveness of the cure thus described, and have already accomplished a number of perfect cures in the testing of the remedy, I do not wish to be limited to any particular action of any ingredient or mixture or compound of ingredients named. So far as I have been able to ascertain, the mercury acts as a germicidal cholagogue, and the opium tends to retard the peristalsis of the intestines and also as a direct curative agent on lesions. The opium also serves to avoid irritation and pain which might otherwise result from the mercury, and at the same time it lessens the rapidity of the action of the mercury, so as to afford a greater opportunity for absorption. The mercury acts directly to destroy the spirochæta and its continuous use to the point of complete cure is rendered possible by the utilization of the other agents named therewith. The quinine serves to stimulate the secretions and promote absorption of the mercury, and also increases the tone of the bowels through its tonic effect. The quinine also has an antitoxic effect. It is, of course, understood that the greater the absorption of mercury the shorter the life of the disease and the briefer the time required for treatment and cure. The licorice powder is employed particularly for the purpose of sweetening the stomach contents and to prevent nausea that might result from the quinine and opium. The malt extract is used simply to convert the ingredients into a mass and to render the contents more palatable.

The use of this invention does not lead to the habitual use or any craving for opium.

Since chemical analyses of the product obtained in the bringing together of the substances as above stated have as yet failed to disclose whether or not a compound or a mixture is produced and whether or not all of the substances employed appear in the final product in the proportions initially introduced, and since variation may be accomplished by oxidation or other chemical reaction probably without material deviation from the therapeutical effects, the appended claims recite the initially introduced substances with the intent to cover their final condition incident to their admixture, however varied therefrom by compounding or other chemical reaction.

What I claim is:—

1. A remedy for internal use for venereal diseases comprising the product incident to the admixture of a germicidal cholagogue, an ingredient adapted to serve as a soothing agent, and an ingredient adapted to serve as a stimulant, the said several ingredients being in substantially the quantity and bearing that relative proportion to each other fixed by the limits of the therapeutical action required substantially as described.

2. A remedy for internal use for venereal diseases comprising the product incident to the admixture of mercury, an ingredient adapted to serve as a soothing agent, and an ingredient adapted to serve as a stimulant, the said several ingredients being in substantially the quantity and bearing that relative proportion to each other fixed by the limits of the therapeutical action required substantially as described.

3. A remedy for internal use for venereal diseases comprising the product incident to the admixture of mercury, an ingredient adapted to serve as a stimulant, an ingredient adapted to serve as a soothing agent, and an ingredient adapted to serve to prevent nausea, the said several ingredients being in substantially the quantity and bearing that relative proportion to each other fixed by the limits of the therapeutical action required substantially as described.

4. A remedy for internal use for venereal diseases comprising the product incident to the admixture of mercury, an ingredient adapted to serve as an agent for repressing peristalsis and an ingredient adapted to serve as a stimulant, the said several ingredients being in substantially the quantity and bearing that relative proportion to each other fixed by the limits of the therapeutical action required substantially as described.

5. A remedy for internal use for venereal diseases comprising the product incident to the admixture of mercury, an ingredient adapted to serve as an agent for repressing peristalsis, and quinine, the said several ingredients being in substantially the quantity and bearing that relative proportion to each other fixed by the limits of the therapeutical action required substantially as described.

6. A remedy for internal use for venereal diseases comprising the product incident to the admixture of mercury, an ingredient adapted to serve as a stimulant, and opium, the said several ingredients being in substantially the quantity and bearing that relative proportion to each other fixed by the limits of the therapeutical action required substantially as described.

7. A remedy for internal use for venereal diseases comprising the product incident to the admixture of mercury, an ingredient adapted to serve as a stimulant, an ingredient adapted to serve as a soothing agent, and licorice, the said several ingredients being in substantially the quantity and bearing that relative proportion to each other fixed by the limits of the therapeutical action required substantially as described.

8. A remedy for internal use for venereal diseases comprising the product incident to the admixture of mercury, opium, and quinine, the said several ingredients being in substantially the quantity and bearing that relative proportion to each other fixed by the limits of the therapeutical action required substantially as described.

9. A remedy for internal use for venereal diseases comprising the product incident to the admixture of parts the substantial equivalent in therapeutical action of and proportioned to be equal substantially to that percentage represented by two thirty-seconds of a grain of opium, thirty-two thirty-seconds of a grain of pulvis pill hydrarge, and ten thirty-seconds of a grain of sulphate of quinine.

10. A remedy for internal use for venereal diseases comprising the product incident to the admixture of parts the substantial equivalent in therapeutical action of and proportioned to be equal substantially to that percentage represented by four thirty-seconds of a grain of opium, forty-eight thirty-seconds grains of pulvis pill hydrarge, and sixteen thirty-seconds of a grain of sulphate of quinine.

11. A remedy for internal use for venereal diseases comprising the product incident to the admixture of mercury, opium, quinine, and licorice, the said several ingredients being in substantially the quantity and bearing that relative proportion to each other fixed by the limits of the therapeutical action required substantially as described.

12. A remedy for internal use for venereal diseases comprising tablets formed of the product incident to the admixture of parts the substantial equivalent in therapeutical action of and proportioned to be equal substantially to that percentage represented by thirty-two tablets made from a substance resulting from the intermixture of the following parts: pulverized opium, grains II; pulvis pill hydrarge, grains XXXII; quinine sulphate, grains X; licorice powder, grains X; extract malt, Qs. mass.

13. A remedy for internal use for venereal diseases comprising tablets formed of the product incident to the admixture of parts the substantial equivalent in therapeutical action of and proportioned to be equal substantially to that percentage represented by thirty-two tablets made from a substance resulting from the intermixture of the following parts: pulverized opium, grains IV; pulvis pill hydrarge, grains XLVIII; quinine sulphate, grains XVI; licorice powder, grains XX; extract malt, Qs. mass.

In testimony whereof I affix my signature in presence of two witnesses.

WILLIAM E. CRAIG.

Witnesses:

J. C. AMMERMAN,

THORNTON L. BROWN.